(12) United States Patent
Webb et al.

(10) Patent No.: US 7,235,583 B1
(45) Date of Patent: Jun. 26, 2007

(54) FATTY ACID-ANTICANCER CONJUGATES AND USES THEREOF

(75) Inventors: Nigel L. Webb, Bryn Mawr, PA (US); Matthews O. Bradley, Laytonsville, MD (US); Forrest Anthony, Villanova, PA (US); Mark Fisher, King of Prussia, PA (US)

(73) Assignee: Luitpold Pharmaceuticals, Inc., Shirley, NY (US)

( * ) Notice: Subject to any disclaimer, the term of this patent is extended or adjusted under 35 U.S.C. 154(b) by 0 days.

(21) Appl. No.: 09/265,307

(22) Filed: Mar. 9, 1999

(51) Int. Cl.
*A61K 31/337* (2006.01)
*C07D 305/14* (2006.01)

(52) U.S. Cl. ............. 514/449; 549/510; 549/511
(58) Field of Classification Search ............ 514/449; 549/510, 511
See application file for complete search history.

(56) References Cited

U.S. PATENT DOCUMENTS

| | | | |
|---|---|---|---|
| 4,088,646 A | 5/1978 | Ishida et al. ............. 544/313 |
| 4,550,109 A | 10/1985 | Folkers et al. ............. 514/249 |
| 4,636,494 A | 1/1987 | Growden et al. ............. 514/78 |
| 4,692,441 A | 9/1987 | Alexander et al. ............. 514/194 |
| 4,729,989 A | 3/1988 | Alexander ............. 514/192 |
| 4,788,063 A | 11/1988 | Fisher et al. ............. 424/449 |
| 4,814,470 A | 3/1989 | Colin et al. ............. 514/449 |
| 4,857,653 A | 8/1989 | Colin et al. ............. 549/511 |
| 4,902,505 A | 2/1990 | Pardridge et al. ............. 424/85.7 |
| 4,933,324 A | 6/1990 | Shashoua ............. 514/17 |
| 4,939,174 A | 7/1990 | Shashoua ............. 514/549 |
| 4,943,579 A | 7/1990 | Vishnuvajjala et al. ...... 514/283 |
| 4,968,672 A | 11/1990 | Jacobson et al. ............. 514/46 |
| 5,059,699 A | 10/1991 | Kingston et al. |
| 5,112,596 A | 5/1992 | Malfroy-Camine ............. 424/2 |
| 5,112,863 A | 5/1992 | Hashimoto et al. ......... 514/534 |
| 5,116,624 A | 5/1992 | Horrobin et al. ............. 424/702 |
| 5,120,760 A | 6/1992 | Horrobin ............. 514/458 |
| 5,141,958 A | 8/1992 | Crozier-Willi et al. ....... 514/558 |
| 5,194,654 A | 3/1993 | Hostetler et al. ............. 558/152 |
| 5,214,062 A | 5/1993 | Mark et al. ............. 514/369 |
| 5,216,023 A | 6/1993 | Literati-Nagy et al. ..... 514/538 |
| 5,216,142 A | 6/1993 | Horribin et al. ............. 514/50 |
| 5,223,263 A | 6/1993 | Hostetler et al. ............. 424/450 |
| 5,246,726 A | 9/1993 | Horrobin et al. ............. 424/646 |
| 5,250,722 A | 10/1993 | Bombardelli et al. ....... 560/104 |
| 5,276,020 A | 1/1994 | Horrobin et al. ............. 514/45 |
| 5,278,324 A | 1/1994 | Kingston et al. |
| 5,284,876 A | 2/1994 | Shashoua et al. ............. 514/549 |
| 5,308,832 A | 5/1994 | Garleb et al. ............. 514/2 |
| 5,336,684 A | 8/1994 | Murray et al. ............. 514/449 |
| 5,356,928 A | 10/1994 | Murray et al. ............. 514/449 |
| 5,362,831 A | 11/1994 | Mongelli et al. ............. 526/304 |
| 5,411,947 A | 5/1995 | Hostetler et al. ............. 514/43 |
| 5,447,936 A | 9/1995 | Hausheer et al. ............. 514/283 |
| 5,453,520 A | 9/1995 | Bombardelli et al. ....... 549/510 |
| 5,453,521 A | 9/1995 | Gaullier et al. ............. 549/541 |
| 5,466,841 A | 11/1995 | Horrobin et al. ............. 554/79 |
| 5,468,754 A | 11/1995 | Hausheer et al. ............. 514/283 |
| 5,473,055 A | 12/1995 | Mongelli et al. ............. 530/329 |
| 5,476,954 A | 12/1995 | Bourzat et al. ............. 549/510 |
| 5,484,809 A | 1/1996 | Hostetler et al. ............. 514/449 |
| 5,504,102 A | 4/1996 | Agharkar et al. ............. 514/449 |
| 5,516,800 A | 5/1996 | Horrobin ............. 514/560 |
| 5,534,499 A | 7/1996 | Ansell |
| 5,545,719 A | 8/1996 | Shashoua ............. 530/345 |
| 5,580,556 A | 12/1996 | Horrobin ............. 424/85.4 |
| 5,580,899 A | 12/1996 | Mayhew et al. ............. 514/449 |
| 5,597,719 A | 1/1997 | Freed et al. ............. 435/194 |
| 5,604,216 A | 2/1997 | Horrobin ............. 514/182 |
| 5,654,290 A | 8/1997 | Bayon et al. ............. 514/77 |
| 5,750,572 A | 5/1998 | Bruzzese ............. 514/560 |
| 5,795,909 A | 8/1998 | Shashoua et al. ............. 514/449 |
| 5,827,819 A | 10/1998 | Yatvin et al. ............. 514/2 |
| 5,919,815 A | 7/1999 | Bradley et al. ............. 514/449 |
| 5,925,669 A | 7/1999 | Katz et al. ............. 514/449 |
| 5,955,459 A | 9/1999 | Bradley et al. ............. 514/220 |
| 5,977,174 A | 11/1999 | Bradley et al. ............. 514/549 |
| 5,985,854 A | 11/1999 | Kozak |
| 5,994,392 A | 11/1999 | Shashoua ............. 514/437 |
| 6,077,837 A | 6/2000 | Kozak |
| 6,080,877 A | 6/2000 | Swindell et al. ............. 549/510 |
| 6,136,796 A | 10/2000 | Kozak |
| 6,166,089 A | 12/2000 | Kozak |
| 6,245,811 B1 | 6/2001 | Horrobin et al. |
| 6,281,376 B1 | 8/2001 | Whittaker et al. |
| 6,291,690 B1 | 9/2001 | Mayhew et al. |
| 2001/0006962 A1 | 7/2001 | Myhren et al. |

FOREIGN PATENT DOCUMENTS

| | | |
|---|---|---|
| DE | 2602175 | 7/1976 |
| DE | 422 4737 | 2/1994 |
| EP | 0 030 009 A1 | 6/1981 |
| EP | 0 599 576 A1 | 1/1994 |
| EP | 0 615 752 A1 | 9/1994 |
| EP | 0 693 498 A1 | 1/1996 |
| FR | 2 698 269 A | 8/1997 |
| JP | 75-9469 | 1/1975 |
| JP | 75-427/1983 | 4/1983 |
| JP | 59025327 A | 2/1984 |
| JP | 59-204175 | 11/1984 |

(Continued)

OTHER PUBLICATIONS

International Search Report, PCT/US 00/06160, International Filing Date: Sep. 3, 2000.
Ansari et al., "Fatty acid conjugates of xenobiotics," *Toxicol. Lett.* (1995), 75, 1–17.

(Continued)

*Primary Examiner*—Ba K. Trinh
(74) *Attorney, Agent, or Firm*—Wolf, Greenfield & Sacks, P.C.

(57) ABSTRACT

The invention provides conjugates of fatty acids and anticancer agents useful in treating cancer, and compositions and formulations thereof. Methods for using the conjugates also are provided.

97 Claims, 7 Drawing Sheets

FOREIGN PATENT DOCUMENTS

| | | |
|---|---|---|
| JP | 61204136 | 11/1984 |
| JP | 1153629 A | 6/1989 |
| JP | 1203331 A | 8/1989 |
| JP | 1287022 A | 11/1989 |
| JP | 6016548 A | 1/1994 |
| JP | 6072868 | 3/1994 |
| JP | 8027010 A | 1/1996 |
| JP | 7082146 | 3/1996 |
| JP | 815133 | 6/1996 |
| JP | 8163991 A | 6/1996 |
| JP | 9025231 A | 1/1997 |
| JP | 9030963 | 2/1997 |
| WO | WO 85/00520 | 2/1985 |
| WO | WO 89/07938 | 9/1989 |
| WO | WO 92/20362 | 11/1992 |
| WO | WO 93/11668 | 6/1993 |
| WO | WO 94/07880 | 4/1994 |
| WO | WO 94/11547 | 5/1994 |
| WO | WO 94/12530 | 6/1994 |
| WO | WO 94/13654 | 6/1994 |
| WO | WO 94/22887 | 10/1994 |
| WO | WO 94/24107 | 10/1994 |
| WO | WO 95/01969 | 1/1995 |
| WO | WO 95/13270 | 5/1995 |
| WO | WO 95/13271 | 5/1995 |
| WO | WO 95/33736 | 12/1995 |
| WO | WO 96/01259 | 1/1996 |
| WO | WO 96/04001 | 2/1996 |
| WO | WO 96/12696 | 5/1996 |
| WO | WO 96/27380 | 9/1996 |
| WO | WO 96/34855 | 11/1996 |
| WO | WO 96/34858 | 11/1996 |
| WO | WO 97/44026 | 11/1997 |
| WO | WO 97/44063 | 11/1997 |
| WO | WO 97/44336 | 11/1997 |
| WO | WO 98/17325 | 4/1998 |
| WO | WO 98/32718 | 7/1998 |
| WO | WO 99/52887 | 10/1999 |
| ZA | 9603433 A | 10/1996 |

OTHER PUBLICATIONS

Chen, et al. "Taxol Structure–Activity Relationships: Synthesis and Biological Evaluation of Taxol Analogs Modified at C–7," *Bioorganic & Medicinal Chemistry Letters,* vol. 4, No. 18, pp. 2223–2228, 1994.

de Groot et al., "Synthesis and Biological Evaluation of 2'–Carbamate–Linked and 2'–Carbonate–Linked Prodrugs of Paclitaxel: Selective Activation by the Tumor–Associated Protease Plasmin," *J. Med. Chem.,* 2000, vol. 43, pp. 3093–3102.

Dischino et al., "Synthesis of the Monosodium Salt of Carbon–14 Labeled Paclitaxel (Taxol®) 2'–Ethyl Carbonate 7–Phosphonooxymethyl Ether, a Potential Prodrug of Paclitaxel", *J. of Labelled Compounds and Radiopharmaceuticals,* vol. XXXIX, No. 2, 1997.

Greenwald et al., "Highly Water Soluble Taxol Derivatives: 7–Polyethylene Glycol Carbamates and Carbonates", *J. Org. Chem.* 1995, 60, pp. 331–336.

Halmos et al., "Fatty acid conjugates of 2'–deoxy–5–fluorouridine as prodrugs for the selective delivery of 5–fluorouracil to tumor cells," *Biochem. Pharmacol.* (1992), 44(1), 149–155.

Hong et al., "Nucleoside–ether lipid conjugates as biotransformed prodrugs of antitumor and antiviral nucleosides," *J. Lipid Mediators Cell Signalling* (1994), 19, 159–161.

Pouillart "Role of butyric acid and its derivatives in the treatment of colorectal cancer and hemoglobinopathies," *Life Sci.* (1998), 63(20), 1739–1760.

UEDA, et al. "Synthesis and Antitumor Evaluation of 2'–Oxycarbonylpaclitaxels (Paclitaxel–2'–Carbonates)", *Bioorganic & Medicinal Chemistry Letters,* vol. 4, No. 15, pp. 1861–1864, 1994.

Anel, A., et al., "Increased Cytotoxicity Of Polyunsaturated Fatty Acids On Human Tumoral B And And T–Cell Lines Compared With Normal Lymphocytes", *Leukemia,* (1992), 6(7):680–688.

Anel, B., et al. "Cytotoxicity Of Chlorambucil And Chlorambucil–Fatty Acid Conjugates Against Human Lymphomas And Normal Human Peripheral Blood Lymphocytes", *Biochem Pharmacol,*(1990),40(6):1193–1200.

Begin, M.E., et al., "Differential Killing Of Human Carcinoma Cells Supplemented With N–3 And N–6 Polyunsaturated Fatty Acids", *J Natl Cancer Inst,* (1986), 77(5):1053–1062. (Abstract).

Bourat, et al., "Long Chain Esters of Pipotiazine as Long–Acting Psychotropic Pro–Drug", *Med. Chem. Proc. Int. Symp.* 5th (1976) pp. 105–114.

Burns, C.P., et al., "Effect Of Docosahexaenoic Acid On Rate Of Differentiation Of H1–60 Human Leukemia", *Cancer Res,* (1989), 49:3252–3258.

Carboni et al., "Synthesis of a Photoaffinity Analog of Taxol as an Approach to Identify the Taxol Binding Site on Microtubules", *Journal of Medicinal Chem.* (Sep. 8, 1992).

Chajes, V., et al., "Influence Of N–3 Fatty Acids On The Growth Of Human Breast Cancer Cells In Vitro: Relationship To Peroxides And Vitamin–E", *Breast Cancer Res Treat,* (1995), 34:199–212.

de Antueno, R.J., et al., "In Vitro Effect Of Eicosapentaenoic And Docosahexaenoic Acids On Prostaglandin E2 Synthesis In A Human Lung Carcinoma", *Biochem Int,* (1989), 19(3):489–496.

de Smidt, P.C., et al., "Characteristics Of Association Of Oleoyl Derivatives Of 5–Fluorodeoxy–Uridine And Methotrexate With Low–Density Lipoproteins (Ldl)", *Pharm Res,* (1992), 9(4):565–569.

Deutsch, H.F., et al., "Cytotoxic Effects Of Daunomycin–Fatty Acid Complexes On Rat Hepatoma Cells", *Cancer Res,* (1983), 43:2668–2672.

Dhopeshwarker, G., "Fatty Acid Transport Through the Blood–Brain Barrier", *Biochim Biophys. Acta* 255:572–579, 1972.

D'Orlando, et al., "Citicoline (CDP–Choline): Mechanisms of Action and Effects in Ischemic Brain Injury", *Neurol. Res.* (1995) 17:281–284.

Ehringer, W. et al., "A Comparison Of The Effects Of Linolenic (18:3 Omega 3) And Docosahexaenoic (22:6 Omega 3) Acids On Phospholipid Bilayers", *Chem Phys Lipids,* (1990), 54:79–88.

Falconer, J.S., et al., "Effect Of Eicosapentaenoic Acid And Other Fatty Acids On The Growth In Vitro Of Human Pancreatic Cancer Cell Lines", *Br. J. Cancer,* (1994), 69:826–832.

Ferrari et al., "9–Cis–6,6'–Diapo–Gamma, Gamma–Carotenedioic Acid Derivatives And Pharmaceutical Compositions Containing Them", p. 710. Abs. 20423w, *Chem Abs.* 95(23), Dec. 7, 1981,EP30,009 Jun. 10, 1981 Jun. 10/1981.

Georg et al., "The Medicinal Chemistry of Taxol", in "Taxol Science and Applications" ed. Matthew Suffness. Boca Raton: CRC Press, Inc., 1995, pp. 317–375.

Guffy, M.M., et al., "Effect Of Cellular Fatty Acid Alteration On Adriamycin Sensitivity In Cultured L1210 Murine Leukemia Cells", *Cancer Res*, (1984), 44:1863–1866.

Hesse et al., "Inhibitory Effect of Cholesteryl- γ–Aminobutyrate" Neurolpharmacology, vol. 24, No. 2, pp. 139–146 (1985).

Hesse, et al., "Uptake in brain neurophysiological activity of two lipid esters of gamma–aminobutyric acid" *Neuropharmacol.* 27:6:637–40 (1998).

Higuchi et al., (Editors), Prodrugs as Novel Drug Delivery Systems, Acs Symposium Series, vol. 14, ACS, Washington, 1975, pp. 14–15.

Iwakami, et al., "Inhibition of Arochidonate 5–Lipoxygenase by Phenolic Compounds", Chem. Pharm. Bull. (Japan), 34(9), 3960–3963 (1986).

Jacob, et al., "Synthesis, brain uptake and pharmacological properties of a glyceryl lipid containing GABA and the GABA–T nhibitor, gamma–vinyl–GABA," *J. Med. Chem.* 33:733–6 (1990).

Jacob, et al., γ–Aminobutyric Acid Esters. 1. Synthesis . . . , Journal of Medicinal Chemistry, vol. 28, No. 1, pp. 106–110 (1985).

Jacob, et al., γ–Aminobutyric Acid Esters.3. Synthesis, brain uptake and pharmacological properties of C–18 Glyceryl lipid esters of BAGA with varying degree of unsaturation, *J. Med. Chem.* 30:1573–6, 1987.

Jacobson, K., et al., Adenosine analogs with covalently attached lipids have enhanced potency at A 1–adenosine receptors, *FEBS Letters* 225:1,2:97–102, (1987).

Jenski, L.J., et al., "Docosahexaenoic Acid–Induced Alteration Of Thy–1 And Cd8 Expression On Murine Splenocytes", *Biochim Biophys Acta*, (1995), 1236(1):39–50.

Jenski, L.J., et al., "Omega 3 Fatty Acids Increase Spontaneous Release Of Cytosolic Components From Tumor Cells", *Lipids*, (1991), 26(5):353–358.

Jenski, L.J., et al., "Omega–3 Fatty Acid–Containing Liposomes In Cancer Therapy", *Proc Soc Exp Biol Med*, (1995), 210(3):227–233.

Karmali, R.A., et al., "Effect Of Omega–3 Fatty Acids On Growth Of A Rat Mammary Tumor", *J Natl Cancer Inst* (1984), 73(2):457–461. (Abstract).

Karmali, R., "N–3 Fatty Acids: Biochemical Actions In Cancer", *J. Nutr. Sci. Vitaminol. (Tokyo)*, (1992), 148–152. (Abstract).

Kinsella, J.E., et al., "Effects Of Polyunsaturated Fatty Acids On The Efficacy Of Antineoplastic Agents Toward L5178y Lymphoma Cells", *Biochem Pharmacol*, (1995), 45(9):1881–1887. (Abstract).

Lohr, et al., "Neuroleptic–Induced Movement Disorders . . . ", Psychiatry, vol. 3, (1989).

Madhavi, N., et al., "Effect Of N–6 And N–3 Fatty Acids On The Survival Of Vincristine Sensitive And Resistant Human Cervical Carcinoma Cells In Vitro", *Cancer Lett*, (1994), 84:31–41.

Makimo, et al., Chemical Abstracts, vol. 106, No. 12, (90177x) issued Mar. 23, 1987, "Pharmaceuticals Permeable to Blood–Brain Barrier".

Mazumdar, et al., "Preparation and Evaluation of Ethambutol Derivatives", Indian J. Pharm. Sci. 47(6): 179–180 (1985).

Minami, M., et al., "Effects Of Low–Dose Eicosapentaenoic Acid, Docosahexaenoic Acid And Dietary Fat On The Incidence, Growth And Cell Kinetics Of Mammary Carcinomas In Rats", *Oncology*, (1996), 53(5):398–405.

Nicolaou et al., "Design, Synthesis and Biological Activity of Protaxols", *Nature*, 364: 464–466, Jul. 1993.

Nishio, et al., "Novel Water–soluble Derivatives of Docosahexaenoic Acid Increase Diacyl–Glycerol Production Mediated by Phosphatidylcholine–Specific Phospholipase C", *Proc. Soc. Exp. Biol. Med.* (1993) 203(2):200–208.

Oshima, M., et al., "Effects Of Docosahexaenoic Acid (Dha) On Intestinal Polyp Development In Apc Delta 716 Apc Delta 716 Knockout Mice", *Carcinogenesis*, (1995), 16(11):2605–2607.

Pascale, A.W., et al., "Omega–3 fatty acid modification of membrane structure and function. Alteration by docosahexaenoic acid of tumor cell sensitivity to immune cytolysis", *Nutr Cancer*, (1993), 19(2):147–157.

Plumb, J.A., et al., "Effect Of Polyunsaturated Fatty Acids On The Drug Sensitivity Of Human Tumour Cell Lines Resistant To Either Cisplatin Or Doxorubicin", *Br J Cancer*, (1993), 67:728–733.

Rose, W.C., Preclinical Antitumor Activity of Taxanes, in "Taxol Science and Applications" ed. Matthew Suffness. Boca Raton: CRC Press, Inc., 1995, pp. 317–375.

Shashoua, et al., γ–Aminobutyric Acid Esters.1. Synthesis . . . , *J. of Med. Chem.*, vol. 27, pp. 659–664 (1984).

Shea et al., *Developmental Brain Research*, 21:307–314 (1985).

Specter, R., "Fatty Acid Transport Through the Blood–Brain Barrier.", *J. of Neurochem.*, 50:2:639–643 (1988).

Swindell, et al., "Characterization of the Taxol Structure–Activity Profile for the Locus of the A–Ring Side Chain Side Chain", *Bioorganic & Medicinal Chem. Ltrs.*, vol. 4, No. 12, pp. 1531–1536. (1994).

Tessier, C., et al., "Docosahexaenoic Acid Is A Potent Inhibitor Of Rat Uterine Stromal Cell Proliferation", *Biochem Biophys Res Commun*, (1995), 207(3):1015–1021.

Tinsley, I.J., et al., "Influence Of Dietary Fatty Acids On The Incidence Of Mammary Tumors In The C3h Mouse", Ch3h Mouse, *Cancer Res*, (1981), 41:1460–1465.

Zerouga, M., et al., "Phospholipid Class As A Determinant In Docosahexaenoic Acid's Effect On Tumor Cell Viability", *Anticancer Res*, (1996), 16:2863–2868. (Abstract).

Zijlstra, J.G., et al., "Influence Of Docosahexaenoic Acid In Vitro On Intracellular Adriamycin Concentration In Lymphocytes And Human Adriamycin–Sensitive And Resistant Small–Cell Lung Cancer Cell Lines, And On Cytotoxicity In The Tumor Cell Lines", *Int J Cancer*, (1987), 40:850–856.

PHARMACOKINETIC PARAMETERS

| DRUG | PHARMACOKINETIC PARAMETER | | |
|---|---|---|---|
| | CLEARANCE | PLASMA $t_{1/2}$ (n=3) | VOLUME OF DISTRIBUTION |
| PACLITAXEL | 28.2 ml/min/kg | 4.8±2.6 HRS | 4.3 L/kg |
| TAXOPREXIN | 0.3 ml/min/kg | 4.8±0.1 HRS | 0.058 L/kg |

FIG. 4

DOSE COMPARISONS: PACLITAXEL vs. TAXOPREXIN IN VARIOUS SPECIES

| SPECIES | DOSE (mg/kg)* | | DOSE RATIO: TAXOPREXIN/PACLITAXEL | |
|---|---|---|---|---|
| | TAXOPREXIN | PACLITAXEL | BASED ON WEIGHT | BASED ON TAXANE MOLARITY** |
| MOUSE | MTD=100x5=500 | MTD=20x5=100 | 5 | 3.6 |
| RAT | Est LD40=420 | LD40=85 | 5 | 3.6 |
| DOG | MTD=80 | Est MTD=20 | 4 | 2.9 |
| | | AVERAGE | 4.7 | 3.4 |

* MTD IS MAXIMUM TOLERATED DOSE
**MW OF TAXOPREXIN=1164; MW OF PACLITAXEL=854; MW RATIO=0.73

FIG. 7

FATTY ACID-ANTICANCER CONJUGATES AND USES THEREOF

BACKGROUND OF THE INVENTION

Improving drug selectivity for target tissue is an established goal in the medical arts. In general, it is desirable to deliver a drug selectively to its target, so that dosage and, consequently, side effects can be reduced. This is particularly the case for toxic agents such as anti-cancer agents because achieving therapeutic doses effective for treating the cancer is often limited by the toxic side effects of the anti-cancer agent on normal, healthy tissue. The problems relating to lack of drug selectivity can be exemplified by Taxol.

Taxol® (paclitaxel) was first isolated in 1971 from the bark of *Taxus brevifolia* and was approved in 1992 by the US Food and Drug Administration for treatment of metastatic ovarian cancer and later for breast cancer. Its mechanism of action is believed to involve promoting formation and hyperstabilization of microtubules, thereby preventing the disassembly of microtubules necessary for completion of cell division. It also has been reported that Taxol induces expression of cytokines, affects the activity of kinases and blocks processes essential for metastasis, in as yet uncharacterized mechanisms of action.

Taxol has attracted unusually strong scientific attention, not only because of its unique antiproliferative mechanism of action, but also because it is active against nearly all cancers against which it has been tested and because it has been discovered to be an analog of numerous closely related compounds occurring naturally. These compounds, taxanes, are now recognized as a new class of anticancer compounds.

Taxol's strength against cancers of diverse tissue origin also represents a significant drawback. An ideal anticancer agent has tissue specificity, thereby reducing side-effects on normal (dividing) cells. Taxol analogs with tissue specificity therefore are desired. Another drawback of Taxol is its extreme insolubility. Taxol can be administered effectively in a solvent including Cremophor® EL (polyoxyethylated castor oil), which combination can provoke severe hypersensitive immune responses. As a result of these drawbacks, and also as a result of the potential for modifying Taxol at numerous sites as demonstrated by other naturally-occurring taxanes with anticancer activity, a search for more selective taxanes was launched.

To date, more than 200 taxanes have been synthesized (or isolated) and tested in vitro or in vivo for anticancer activity. The results, however, have been so disappointing that the National Cancer Institute (NCI) generally no longer is interested in testing Taxol analogs. In general with Taxol analogs, the solubility problems remain, and/or potency is sharply reduced, and/or selectivity is not improved, and/or the ratio of the median toxic dose to the median effective dose ("therapeutic index") is unacceptably reduced.

Taxol has the following formula:

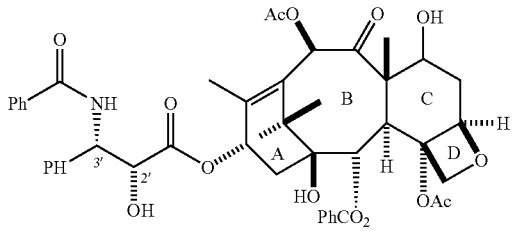

Taxanes have the basic three ring structure (A, B and C), substituted or unsubstituted.

Taxol's carbons are numbered conventionally as follows:

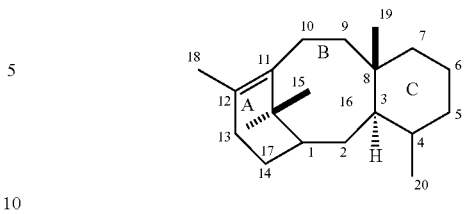

Based upon the taxanes tested to date, as many questions have been raised as have been answered, and general rules have not been fashioned easily in predicting selectivity, activity and solubility. Firstly, no rules have emerged regarding selectivity. Those taxanes that are strongly active appear to have activity as broad as Taxol's activity, and no headway appears to have been made in terms of developing a more selective Taxol analog.

Some information about activity has emerged. Numerous substitutions have been made at C7, C9, C10, C19, $R_1$ and combinations thereof while retaining significant, but usually reduced, activity. Substitutions at C2, C4 and 2'OH, however, are generally not tolerated. These conclusions are only generalities, for example, because some substitutions at C9–C10 (cyclic derivatives) are not tolerated and some substitutions at C2 (meta substitutions on the phenyl) are tolerated. Likewise, the C13 side chain and, in particular, the 2'OH are required, although the minimum structural requirements of the side chain have not been determined for therapeutic efficacy.

Attempts to improve Taxol's solubility have not resulted in successful clinical products. One approach has been to manufacture prodrugs of Taxol, which prodrugs undergo in vivo transformation into Taxol and some other product. Attempts were made to esterify the C7 hydroxy and 2' hydroxy groups, with the hope that the bond would be stable in solution (to permit preferred administration modes—i.v. over at least 24 hours) but would cleave readily in vivo. The groups tested were all hydrophilic and included amines, short carboxylic acids (using e.g. succinic anhydride and glutaric anhydride), sulfonic acids, amino acids and phosphates. Generally, activity was reduced although some success was obtained with certain derivatives. Again, no particular pattern emerged permitting one to predict reliably which groups could be substituted on Taxol to yield a therapeutically useful product, although it was suggested that the 2' OH derivatives may cleave more easily than the C7 OH derivatives.

Several other factors add to the problem of predicting which Taxol analogs will be effective. Multiple mechanisms of action have been proposed in the literature, and a change in one position may have no effect on activity on one such mechanism but may eliminate activity on another mechanism. In addition, changes that favorably influence activity may unfavorably influence bioavailability. For example, Taxol affects microtubule formation inside a cell, but a change in structure that increases intracellular activity may adversely affect the ability of Taxol to gain entry into a cell. Taxol also is known to bind to proteins, and the effect on activity that results from a change in Taxol's binding to protein (in terms of conformation, cellular absorption and solubility) is unknown.

It has been reported that Taxol does not get into the brain, apparently excluded by the blood brain barrier. It is not known why this is so, as Taxol is lipophilic, gets into cells and might be expected to cross the blood brain barrier.

Among the most promising of the two hundred analogs tested is Taxotere® (docetaxel), because of its slightly increased activity and solubility. Oddly, however, Taxotere differs from Taxol at sites which typically do not have a strong influence on activity, and one would not predict the improvements in Taxotere from these differences, even in hindsight.

Taxotere has the following formula:

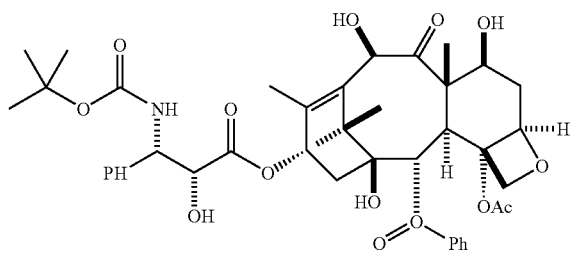

Fatty acids previously have been conjugated with drugs to help the drugs as conjugates cross the blood brain barrier. DHA (docosahexaenoic acid) is a 22 carbon naturally-occurring, unbranched fatty acid that previously has been shown to be unusually effective, when conjugated to a drug, in crossing the blood brain barrier. DHA is attached via the acid group to hydrophilic drugs and renders these drugs more hydrophobic (lipophilic). DHA is an important constituent of the brain and recently has been approved as an additive to infant formula. It is present in the milk of lactating women. The mechanism of action by which DHA helps drugs conjugated to it cross the blood brain barrier is unknown.

Another example of the conjugation of fatty acids to a drug is the attachment of pipotiazine to stearic acid, palmitic acid, enanthic acid, undecylenic acid or 2,2-dimethyl-palmitic acid. Pipotiazine is a drug that acts within the central nervous system. The purpose of conjugating pipotiazine to the fatty acids was to create an oily solution of the drug as a liquid implant for slow release of the drug when injected intramuscularly. The release of the drug appeared to depend on the particular fatty acid selected, and the drug was tested for its activity in the central nervous system.

Lipidic molecules, including the fatty acids, also have been conjugated with drugs to render the conjugates more lipophilic than the drug. In general, increased lipophilicity has been suggested as a mechanism for enhancing intestinal uptake of drugs into the lymphatic system, thereby enhancing the entry of the conjugate into the brain and also thereby avoiding first-pass metabolism of the conjugate in the liver. The type of lipidic molecules employed have included phospholipids, non-naturally occurring branched and unbranched fatty acids, and naturally occurring branched and unbranched fatty acids ranging from as few as 4 carbon atoms to more than 30 carbon atoms. In one instance, enhanced receptor binding activity was observed (for an adenosine receptor agonist), and it was postulated that the pendant lipid molecule interacted with the phospholipid membrane to act as a distal anchor for the receptor ligand in the membrane micro environment of the receptor. This increase in potency, however, was not observed when the same lipid derivatives of adenosine receptor antagonists were used, and generalizations thus were not made possible by those studies.

SUMMARY OF THE INVENTION

According to one aspect of the invention, a fatty acid-anticancer compound conjugate composition for administration to a subject is provided. The composition includes at least one fatty acid-anticancer compound conjugate in a container for administration to a subject. The amount of the fatty acid-anticancer compound in the container is at least about 10% greater than the maximum tolerated dose (MTD) for the unconjugated at least one anticancer compound. Preferably the amount of the fatty acid-anticancer compound in the container is at least about 20% greater than the MTD, 30% greater than the MTD 40% greater than the MTD, 50% greater than the MTD, 75% greater than the MTD, 100% greater than the MTD, 200% greater than the MTD, 300% greater than the MTD, or 400% greater than the MTD for the unconjugated at least one anticancer compound. In certain preferred embodiments, the container is a container for intravenous administration. In other preferred embodiments, the anticancer compound is a taxane, particularly paclitaxel or docetaxel. It is preferred that the conjugate is not encapsulated in a liposome.

According to still another aspect of the invention, methods for treating a subject having an abnormal mammalian cell proliferative disorder are provided. The methods include administering a composition including at least one fatty acid-anticancer compound conjugate to the subject in an amount which is at least about 10% greater than the maximum tolerated dose (MTD) for the unconjugated at least one anticancer compound. Preferably the amount of the at least one fatty acid-anticancer compound administered is at least about 20% greater than the MTD, 30% greater than the MTD, 40% greater than the MTD, 50% greater than the MTD, 75% greater than the MTD, 100% greater than the MTD, 200% greater than the MTD, 300% greater than the MTD, or 400% greater than the MTD for the unconjugated at least one anticancer compound. In other preferred embodiments, the anticancer compound is a taxane, particularly paclitaxel or docetaxel. It is preferred that the conjugate is not encapsulated in a liposome.

In still another aspect of the invention, kits for administration of a fatty acid-anticancer compound conjugate composition to a subject is provided. The kits include a container containing a composition which includes at least one fatty acid-anticancer compound conjugate, and instructions for administering the at least one fatty acid-anticancer compound conjugate to subject in need of such treatment in an amount which is at least about 10% greater than the maximum tolerated dose (MTD) for the unconjugated at least one anticancer compound. Preferably the subject has an abnormal mammalian cell proliferative disorder. Preferably the amount of the at least one fatty acid-anticancer compound conjugate to be administered is at least about 20% greater than the MTD, 30% greater than the MTD, 40% greater than the MTD, 50% greater than the MTD, 75% greater than the MTD, 100% greater than the MTD, 200% greater than the MTD, 300% greater than the MTD, or 400% greater than the MTD for the unconjugated at least one anticancer compound. In certain preferred embodiments, the container is a container for intravenous administration. In other preferred embodiments, the anticancer compound is a taxane, particularly paclitaxel or docetaxel. It is preferred that the conjugate is not encapsulated in a liposome.

A method for increasing the therapeutic index of anticancer compounds in a subject is provided according to another aspect of the invention. The method includes conjugating a fatty acid to an anticancer compound to form a fatty acid-anticancer compound conjugate; and administering the fatty acid-anticancer compound conjugate to the subject. The therapeutic index of the anticancer compound thus administered is improved relative to non-conjugated formulations of the anticancer compound. Preferably the subject has an abnormal mammalian cell proliferative disorder, and the subject preferably is human. In certain embodiments, the anticancer compound is a taxane, preferably paclitaxel or docetaxel. It is preferred that the conjugate is not encapsulated in a liposome.

According to another aspect of the invention, methods for administering a fatty acid-anticancer compound conjugate to a subject in need of such treatment are provided. The method includes infusing the conjugate in fewer than 3 hours. Preferably the conjugate is infused in 2 hours or less. Preferably the subject has an abnormal mammalian cell proliferative disorder, and the subject preferably is human. In certain embodiments, the anticancer compound is a taxane, preferably paclitaxel or docetaxel. It is preferred that the conjugate is not encapsulated in a liposome.

In the foregoing methods, it is preferred that a dose of a fatty acid-conjugated anticancer compound is administered which exceeds the maximum tolerated dose of the unconjugated anticancer compound.

According to one aspect of the invention, an injectable preparation of at least one fatty acid-taxane conjugate composition is provided. The preparation includes greater than about 6 mg/ml of the at least one fatty acid-taxane conjugate composition. Preferably, the preparation includes greater than about 7 mg/ml, 8 mg/ml, 10 mg/ml, 15 mg/ml, 20 mg/ml, 40 mg/ml, 60 mg/ml, 80 mg/ml, or 100 mg/ml of the at least one fatty acid-taxane conjugate composition. Preferred taxanes include paclitaxel and docetaxel.

The invention also provides an injectable composition of at least one fatty acid-taxane conjugate which includes less than about 0.3 mg/ml of the at least one fatty acid-taxane conjugate. Preferably the composition includes less than about 0.275, 0.25, 0.225, 0.2, 0.15, or 0.1 mg/ml of the at least one fatty acid-taxane conjugate. Preferred taxanes include paclitaxel and docetaxel.

According to another aspect of the invention, fatty acid-taxane conjugate compositions are provided. The compositions include an amount of at least one fatty acid-taxane conjugate greater than about 6 mg/ml. The compositions also include a surfactant. Preferably the compositions include greater than about 7 mg/ml, 8 mg/ml, 10 mg/ml, 15 mg/ml, 20 mg/ml, 40 mg/ml, 60 mg/ml, 80 mg/ml, or 100 mg/ml of the at least one fatty acid-taxane conjugate. Preferred taxanes include paclitaxel and docetaxel.

In certain embodiments, the surfactant in the fatty acid-taxane conjugate compositions is Cremophor EL or EL-P. Preferably the concentration of Cremophor is between about 9.6% and about 49.7% (vol/vol).

In yet another aspect of the invention, other fatty acid-taxane conjugate compositions are provided. The compositions include at least about 37 mg/ml of at least one fatty acid-taxane conjugate. Preferably, the compositions include at least about 40 mg/ml, 50 mg/ml, 60 mg/ml, 80 mg/ml, or 100 mg/ml of the at least one fatty acid-taxane conjugate. Preferably the taxane is paclitaxel or docetaxel.

According to still another aspect of the invention, fatty acid-taxane conjugate compositions are provided which have certain ratios between the amount of the fatty acid-taxane conjugates and volume of surfactant. The compositions include at least one fatty acid-taxane conjugate and a surfactant; the ratio of the weight of the at least one fatty acid-taxane conjugate and volume of the surfactant is at least about 50 mg/ml. Preferably the ratio of the weight of the at least one fatty acid-taxane conjugate and volume of the surfactant is at least about 60 mg/ml, 70 mg/ml, 80 mg/ml, 90 mg/ml, or 100 mg/ml. The preferred surfactants include Cremophor EL and EL-P, and the preferred taxanes include paclitaxel or docetaxel. In other embodiments, the compositions include a solvent, preferably ethanol; the preferred ratio of surfactant to solvent is about 1:1.

In still another aspect of the inventions, fatty acid-taxane conjugate compositions are provided which have certain ratios between the amount of the fatty acid-taxane conjugate and volume of solvent. The compositions include at least one fatty acid-taxane conjugate and a solvent; the ratio of the weight of the at least one fatty acid-taxane conjugate and volume of the solvent is at least about 42 mg/ml. Preferably the ratio of the weight of the at least one fatty acid-taxane conjugate and volume of the solvent is at least about 50 mg/ml, 60 mg/ml, 70 mg/ml, 80 mg/ml, 90 mg/ml, or 100 mg/ml. The preferred solvents include ethanol, and the preferred taxanes include paclitaxel or docetaxel. In other embodiments, the compositions include a surfactant, preferably Cremophor EL of EL-P; the preferred ratio of surfactant to solvent is about 1:1.

According to another aspect of the invention, compositions of fatty acid-taxane conjugates which include solvent and surfactant are provided. The compositions include between about 7 and about 120 milligrams of a fatty acid-taxane conjugate, between about 40% and 100% of solvent, and between about 1% and about 60% surfactant. In preferred embodiments, the compositions include between about 20 mg and about 120 mg of a fatty acid-taxane conjugate, between about 40% and 100% of solvent, and between about 1% and about 60% surfactant. More preferably, compositions include between about 35 mg and about 45 milligrams of a fatty acid-taxane conjugate, between about 45% and about 55% of solvent, and between about 45% and about 55% surfactant. In particularly preferred embodiments, the compositions include between about 6 mg and about 20 milligrams of a fatty acid-taxane conjugate, between about 5% and about 15% of solvent, and between about 5% and about 15% surfactant, or between about 6 mg and about 12 milligrams of a fatty acid-taxane conjugate, between about 8% and about 12% of solvent, and between about 8% and about 12% surfactant, or between about 1 mg and about 5 milligrams of a fatty acid-taxane conjugate, between about 1% and about 10% of solvent, and between about 0.5% and about 4% surfactant. Preferably the solvent is ethanol and the surfactant is Cremophor EL or EL-P.

For all of the foregoing, the fatty acid is preferably a C8–C26 unbranched, naturally occurring fatty acid. More preferably, the fatty acid is selected from the group consisting of C8:0 (caprylic acid), C10:0 (capric acid), C12:0 (lauric acid), C14:0 (myristic acid), C16:0 (palmitic acid), C16:1 (palmitoleic acid), C16:2, C18:0 (stearic acid), C18:1 (oleic acid), C18:1-7 (vaccenic), C18:2-6 (linoleic acid), C18:3-3 (α-linolenic acid), C18:3-5 (eleostearic), C18:3-6 (β-linolenic acid), C18:4-3, C20:1 (gondoic acid), C20:2-6, C20:3-6 (dihomo-y-linolenic acid), C20:4-3, C20:4-6 (arachidonic acid), C20:5-3 (eicosapentaenoic acid), C22:1 (docosenoic acid), C22:4-6 (docosatetraenoic acid), C22:5-6 (docosapentaenoic acid), C22:5-3 (docosapentaenoic), C22:6-3 (docosahexaenoic acid) and C24:1-9 (nervonic). Particularly preferred is docosahexaenoic acid.

In the foregoing compositions, products and methods, ranges of doses, ratios, and amounts have been given. The ranges include the numbers specifically set forth as well as each andevery number therebetween. Thus, for example, when an amount of a fatty acid-taxane conjugate is specified as "greater than about 6 mg/ml, 7 mg/ml, 8 mg/ml, 10 mg/ml, 15 mg/ml, 20 mg/ml, 40 mg/ml, 60 mg/ml, 80 mg/ml, 100 mg/ml," the range includes conjugates in the amounts of 6, 7, 8, 9, 10, 11, 12, 13, 14, 15, 16, 17, 18, 19, 20, and so on including each number throughout the range.

BRIEF DESCRIPTION OF THE DRAWINGS

FIG. 4 is a table depicting the pharmacokinetic parameters of taxoprexin and paclitaxel;

FIG. 7 is a table depicting dose comparisons (MTD and Est $LD_{40}$) of taxoprexin and paclitaxel in various species.

Figure 1:
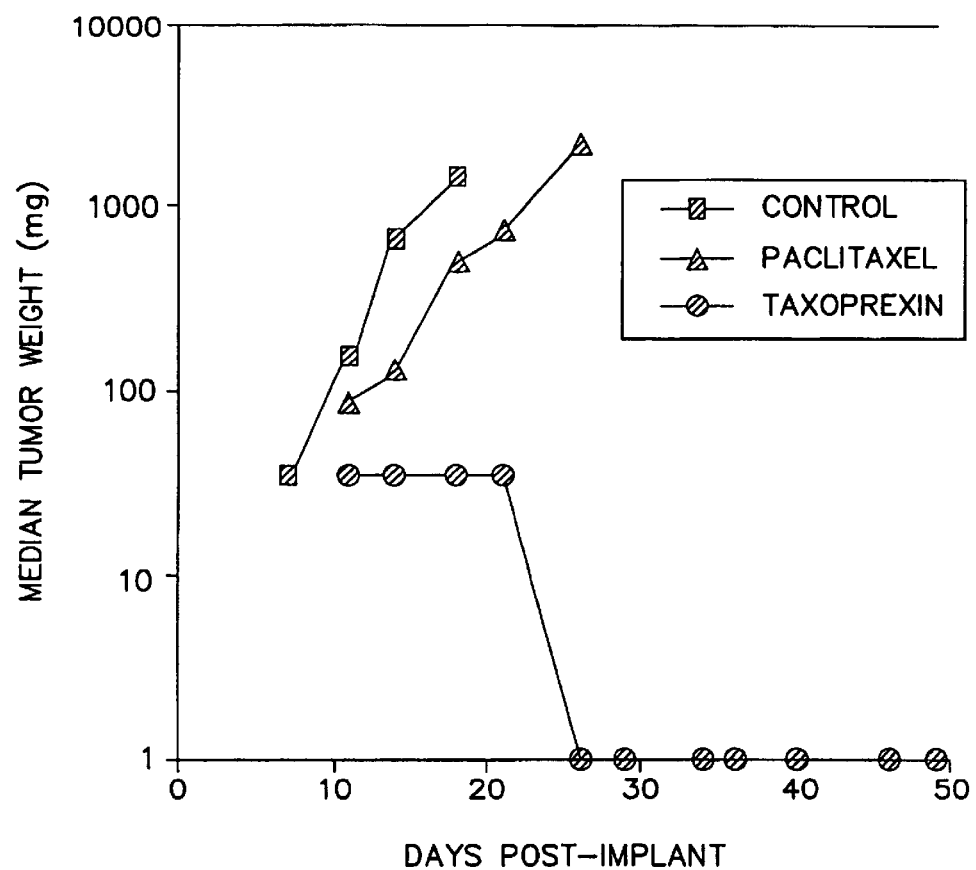
FIG. 1 is a graph depicting the effects of taxoprexin and paclitaxel against M 109 lung carcinoma in mice.

DETAILED DESCRIPTION OF THE INVENTION cis-docosahexaenoic acid (DHA) is a naturally occurring fatty acid. It is an unbranched chain fatty acid with six double bonds, all cis. Its structure is as follows:

DHA can be isolated, for example, from fish oil or can be chemically synthesized. These methods, however, can generate trans isomers, which are difficult and expensive to separate and which may present safety problems in humans. The preferred method of production is biological synthesis to produce the all cis isomer. The preferred source of DHA is from Martek Biosciences Corporation of Columbia, Md. Martek has a patented system for manufacturing DHA using microalgae which synthesize only a single isomer of DHA, the all cis isomer. Martek's patents include U.S. Pat. Nos. 5,374,657, 5,492,938, 5,407,957 and 5,397,591.

DHA also is present in the milk of lactating women, and Martek's licensee has obtained approval in Europe of DHA as a nutritional supplement for infant formula.

It is known that DHA can be unstable in the presence of oxygen. To stabliize DHA and its conjugates it is important to add anti-oxidants to the material after it is synthesized. One method of stablization is to make-up the newly synthesized material in the following solution: 100 g neat DHA-taxol plus 100 g of vehicle (100ml propylene glycol, 70 mg α-tocopherol, 5 mg dialaurylthiodipropionic acid, 50 mg ascorbic acid)prepared and held under argon in amber, sealed vials and stored at four degrees centigrade. The following anti-oxidants may also be employed: ascorbic acid, ascorbyl palmitate, dilauryl ascorbate, hydroquinone, butyated hydroxyanisole, sodium meta bisulfite, t-B carotene and α-tocopherol. A heavy metal chelator such as ethylenediamine tetra-acetic acid (EDTA) may also be used.

Paclitaxel was first isolated from the bark of *Taxus brevifolia* (Wani et al., *J. Am. Chem. Soc.*, 93, 2325, 1971).

Its isolation and synthesis have been reported extensively in the literature. Applicants obtained paclitaxel from a commercial source, Hauser Laboratories, of Boulder, Colo.

The prefered compound of the invention, "Taxoprexin™", is a covalent conjugate of DHA and paclitaxel. Its chemical structure, synthesis, purification and in vitro action are described in U.S Pat. No. 5,795,909, the entire disclosure of which is incorporated by reference herein. The structure is shown as "conjugate 1" in Example 1 of that patent.

The maximum tolerated dose (MTD) for any therapeutic compound is identified as part of its clinical evaluation. For example, phase I trials can include a determination of the maximum tolerated dose, dose limiting toxicities (DLT) and pharmacokinetics of a test compound. Thus, the MTD for any Food and Drug Administration (FDA) approved therapeutic compound is known to those of ordinary skill in the art as a matter of the public record. The MTD for any particular therapeutic compound may vary according to its formulation (e.g., injectable formulation, implantable bioerodible polymer formulation, oral formulation), route of delivery (e.g., intravenous, oral, intratumoral), manner of delivery (e.g., infusion, bolus injection), dosing schedule (e.g., hourly, daily, weekly) and the like. MTD frequently is defined as the highest dose level at which 50% of subjects administered with the drug develop a dose limiting toxicity. Other definitions which are clinically relevant and generally accepted will be known to one of ordinary skill in the art.

Measurement of maximum tolerated dose may be expressed as weight of drug per weight of subject, weight of drug per body surface area, etc. The MTD of anticancer compounds is frequently expressed as weight per square meters ($mg/m^2$) of body surface area. For example, the MTD for paclitaxel infusion in humans is 225 $mg/m^2$. MTD also may be expressed as a dose relative to a time component, such as weight of drug per body surface area per day.

For therapeutics which have not yet been subjected to human clinical trails, or subjected to any determination of the MTD in humans (e.g., experimental or highly toxic compounds), one of skill in the art can estimate the MTD by using animal models. Calculation of MTD in animals may be based on a number of physiological parameters, such as death, particular toxicities, drug induced weight loss. Using death as an endpoint, the MTD may be the dose given test animals in which each member of the test group survived. Using toxicity as an endpoint, the MTD may be the dose at which moderate but not severe toxicity is observed. Using weight loss as an endpoint, the MTD may be the dose above which a certain percent change in body weight is induced. Other methods for determining MTDs using animal models and various endpoints are known to one of ordinary skill in the art. Correlation of animal MTDs to human MTDs for a therapeutic compound is an accepted practice in the pharmaceutical arts.

Thus the invention in another aspect provides compositions and formulations for administration to a subject, preferably a human subject, containing amounts of a fatty acid-anticancer compound conjugate which exceeds the maximum tolerated dose for the unconjugated anticancer compound. The fatty acid-anticancer compound conjugate preferably is in a container for administration to a subject. Preferably the container is a container for intravenous administration, such as an IV bag.

The amount of the fatty acid-anticancer compound in the container is at least about 10% greater than the MTD for the unconjugated compound. Preferably the amount of the fatty acid-anticancer compound in the container is at least about 20%, 30%, 40%, 50%, 75%, 100%, 200%, 300% or 400% greater than the MTD for the unconjugated at least one anticancer compound. The anticancer compound is preferably a taxane, particularly paclitaxel or docetaxel.

Methods for administering these compositions to subjects having an abnormal mammalian cell proliferative disorder also are provided.

Kits containing fatty acid-anticancer compounds in amounts also are provided. The kits contain one or more containers with the conjugated anticancer compound along with instructions for mixing, diluting and/or administering the anticancer compound in amounts greater than the MTD for the unconjugated anticancer compound. The kits also can include other containers with one or more solvents, surfactants, preservatives and/or diluents (e.g. normal saline (0.9% NaCl), or 5% dextrose (D5W)), as well as containers for mixing, diluting, and/or administering the conjugates to a subject in need of such treatment.

The anticancer compounds in the kit may be provided as liquid solutions, or as dried powders. When the compound provided is a dry powder, the powder may be reconstituted by the addition of a suitable solvent, which also may be provided. Liquid forms of the conjugates may be concentrated (for dilution prior to administration) or ready to administer to a subject.

As noted above, the therapeutic index is the ratio of the median toxic dose to the median effective dose. Conjugation of fatty acids to anticancer compounds to form a fatty acid-anticancer compound conjugate reduces toxicity of the anticancer compounds, and increases effectiveness as compared to the unconjugated anticancer compounds. Therefore the invention also provides methods for increasing the therapeutic index of anticancer compounds in a subject. The methods include conjugating a fatty acid to an anticancer compound to form a fatty acid-anticancer compound conjugate and administering the fatty acid-anticancer compound conjugate to the subject. The therapeutic index of the anticancer compound conjugate is improved relative to unconjugated formulations of the anticancer compound. Preferably the anticancer compound is a taxane, particularly paclitaxel or docetaxel.

Although the conjugate may be encapsulated in a liposome, it is preferred that the conjugate is not encapsulated by a liposome. The preferred subjects for the method are humans.

The conjugated anticancer compounds described herein are less toxic and more effective than the corresponding unconjugated anticancer compounds. Therefore the fatty acid-anticancer compound conjugates can be administered in amounts which are equally toxic but more effective, or in doses which are equally effective and less toxic than the corresponding unconjugated anticancer compounds. In general, conjugation of fatty acids to anticancer compounds permits an increase in the maximum tolerated dose relative to unconjugated anticancer compounds.

For example, it has been determined that a conjugate of DHA and paclitaxel (Taxoprexin™) has a maximum tolerated dose in animals (mice, rats and dogs) which is about 4–5 times greater (by weight) than paclitaxel alone or about 3–4 times greater (by molarity) than paclitaxel alone.

The invention provides injectable preparations of at least one fatty acid-taxane conjugate composition. The injectable preparations are prepared for administration to a subject in need of treatment with a taxane, e.g., a subject having cancer. The injectable preparations contain higher concentrations of taxane derivatives than was previously thought possible. For example, present infusion formulations of paclitaxel contain 0.3 mg/ml–1.2 mg/ml diluted in aqueous solution. It has been found, surprisingly, that taxane derivatives having a conjugated fatty acid, as disclosed herein, can be administered at much higher concentrations to subjects without the dose limiting toxicities observed with other taxane formulations. The injectable preparations have greater than about 6 mg/ml of the fatty acid-taxane conjugates described herein. Preferably, the preparations contain greater than about 7 mg/ml, greater than about 8 mg/ml, greater than about 9 mg/ml, greater than about 10 mg/ml, greater than about 12 mg/ml, and so on.

In addition, low-dose injectable preparations of taxanes having lower amounts of taxanes than the formulations presently used clinically are also provided. The surprisingly increased activity of fatty acid-taxane conjugates relative to unconjugated taxanes permits administration of lesser amounts while obtaining the same anticancer activity. Thus, injectable preparations having less than 0.3 mg/ml are provided, which formulations have anticancer acitivity when administered to a subject with cancer. Preferably the low-dose injectable preparations contain less than about 0.25 mg/ml, less than about 0.2 mg/ml, less than about 0.15 mg/ml, less than about 0.1 mg/ml, and so on.

Other compositions are provided which have still higher amounts of fatty acid-taxane conjugates. In some embodiments, the compositions contain greater than about 6 mg/ml of at least one fatty acid-taxane conjugate and a surfactant. Preferably, the compositions contain greater that about 7 mg/ml, greater that about 8 mg/ml, greater that about 9 mg/ml, greater that about 10 mg/ml, greater that about 12 mg/ml, and so on. In other embodiments, the compositions include at least about 37 mg/ml of at least one fatty acid-taxane conjugate. Preferably such compositions contain at least about 40 mg/ml, at least about 50 mg/ml, at least about 60 mg/ml, at least about 80 mg/ml, and at least about 100 mg/ml of at least one fatty acid-taxane conjugate.

The foregoing preparations, formulations and compositions may be encapsulated by liposomes, according to standard procedures for preparation of liposomes, but preferably are not.

All of the compositions herein which contain taxanes or other anticancer compounds optionally can contain additional anticancer compounds. The compositions also can contain other components useful in formulating anticancer compounds for administration to humans, including surfactants, solvents, preservatives, diluents, and the like, all of which are standard in the pharmaceutical arts.

Suitable surfactants for use with the present invention include nonionic agents, such as long-chain fatty acids and their water-insoluble derivatives. These include fatty alcohols such as lauryl cetyl and stearyl alcohol, glyceryl esters such as the naturally occurring mono-, di- and triglycerides, and fatty acid esters of fatty alcohols, such as propylene glycol, polyethylene glycol, sorbitan, sucrose and cholesterol. Also useful are compounds that are those that have polyoxyethylene groups added through an ether linkage with an alcohol group. Compounds that are particularly useful in the present invention include the polyoxyethylene sorbitan fatty acid esters and polyoxyethylene glycerol and steroidal esters. Particularly preferred surfactants are Cremophor® EL and Cremophor® EL-P, which are polyoxyethylated castor oil surfactants.

It is contemplated that other surfactants may be used to solubilize the compositions described herein. For example, it is contemplated that polysorbate 80, polysorbate 20, sodium laurate, sodium oleate, and sorbitan monooleate may be useful in context of the present invention. Anionic surfactants may also be useful in the practice of the present invention. Examples of these include, but are not limited to, sodium cholate, sodium lauryl sulfate, sodium deoxycholate, sodium laurate, sodium oleate, and potassium laurate.

In certain embodiments, dehydrated ethanol is used as a solvent for the compositions described herein. In other embodiments, glycols such as propylene glycol or polyethylene glycol are within the scope of the invention. Simple complex polyols may also be suitable solvents. Moreover, the use of non-dehydrated alcohols may also be suitable within the scope of the present invention. It is recognized that the determination of a solvent and its proper concentration to fully solubilize the fatty acid-anticancer compositions is within the scope of a skilled artisan, and would not require undue experimentation.

For example, a conjugate of DHA and paclitaxel (Taxoprexin™) can be supplied at 100 mg/ml in EtOH. The concentrated conjugate can bediluted diluted 2:3 with a 4:1 Cremophor EL:EtOH surfactant/solvent mixture, resulting in an intermediate solution of 40 mg/ml DHA-paclitaxel in a Cremophor/ EtOH vehicle. This intermediate solution can be diluted 1:5 into an injection vehicle such as normal saline 5% dextrose to give a final composition of 8 mg/ml DHA-paclitaxel in Cremophor/EtOH.

EXAMPLE 1

The Effects of Taxoprexin and Paclitaxel Against M 109 Lung Carcinoma in Mice

Syngeneic mice were injected with mouse lung tumor line M (Madison) 109 sub-cutaneously in the flank. Four days after tumor implantation, when the tumor weighed about 30 mg, taxoprexin (OD=120 mg/kg/day×5 days) or paclitaxel (OD=20 mg/kg/day×5 days) were injected as a bolus through the tail vein on each of five successive days (days 4 through 8). Both drugs were dissolved in 10% cremophor EL/10% ethanol/80% saline. Tumor volume was estimated from tumor width and length. The results show that paclitaxel retarded tumor growth for about four days. In contrast, taxoprexin completely eliminated all measurable tumors in eight out of eight mice. (FIG. 1)

EXAMPLE 2

The Effects of Taxoprexin and Paclitaxel Against M 109 Lung Carcinoma in Mice.

Figure 2:
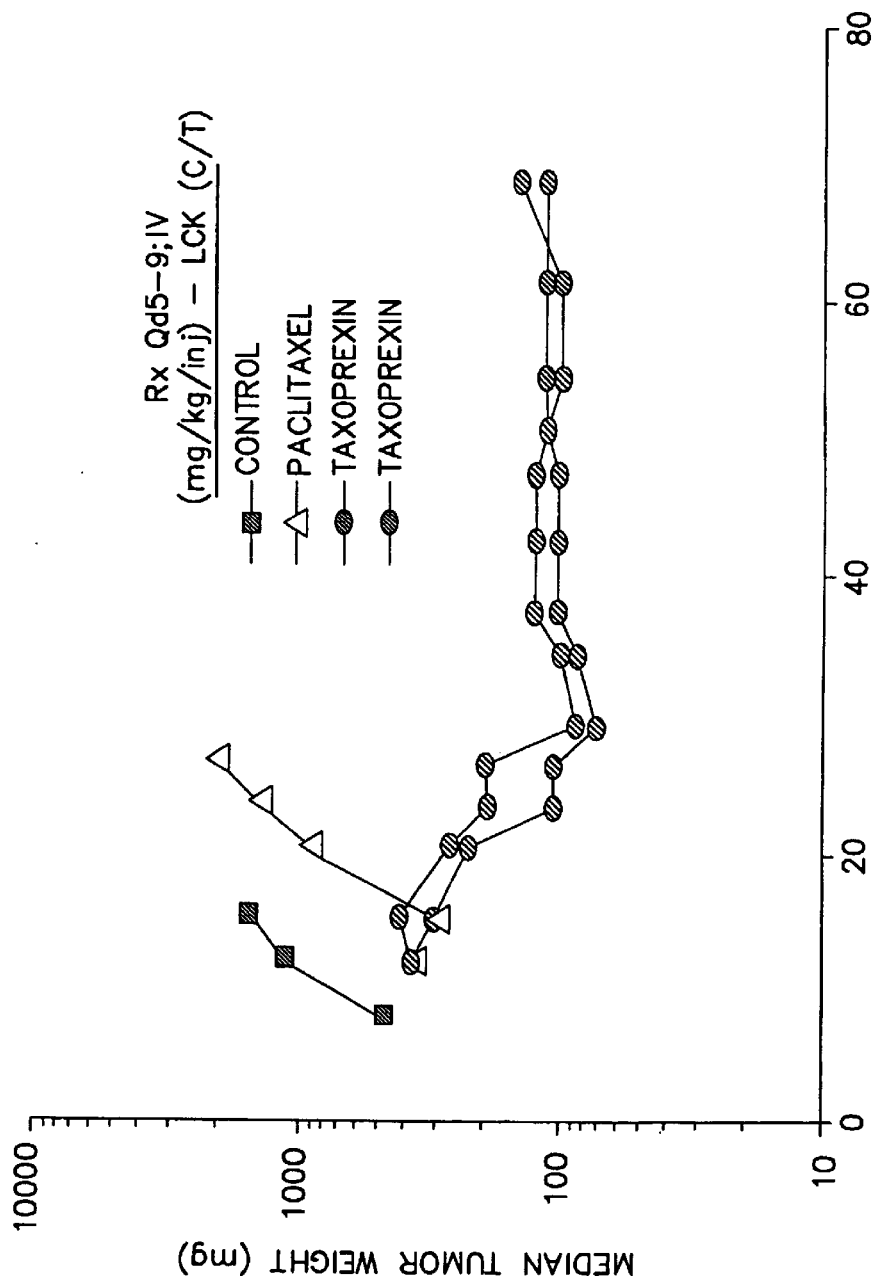
FIG. 2 is a graph depicting the effects of taxoprexin and paclitaxel against M 109 lung carcinoma in mice.

Syngeneic mice were injected with mouse lung tumor line M (Madison) 109 sub-cutaneously in the flank. Five days after tumor implantation, one day later than in the last figure, when the tumors had grown ten-fold larger to 300 mg, taxoprexin (OD=120 mg/kg/day×5 days) or paclitaxel (OD=20 mg/kg/day×5 days) were injected as a bolus through the tail vein on each of five successive days. Both drugs were dissolved in 10% cremophor EL/10% ethanol/80% saline. Tumor volume was estimated from tumor width and length. As in the previous experiment, paclitaxel retarded tumor growth for about four days (LCK=1.0). In contrast, taxoprexin completely eliminated all measurable tumors in seven out of eight mice (C/T=7/8) at 120 mg/kg/day×5 days, and in four out of seven mice at 80 mg/kg/day×5 days. Histological examination of the tissue where the tumors had showed no tumor cells, only scar tissue. These data show that taxoprexin is curative in this model. (FIG. 2)

EXAMPLE 3

Figure 3:
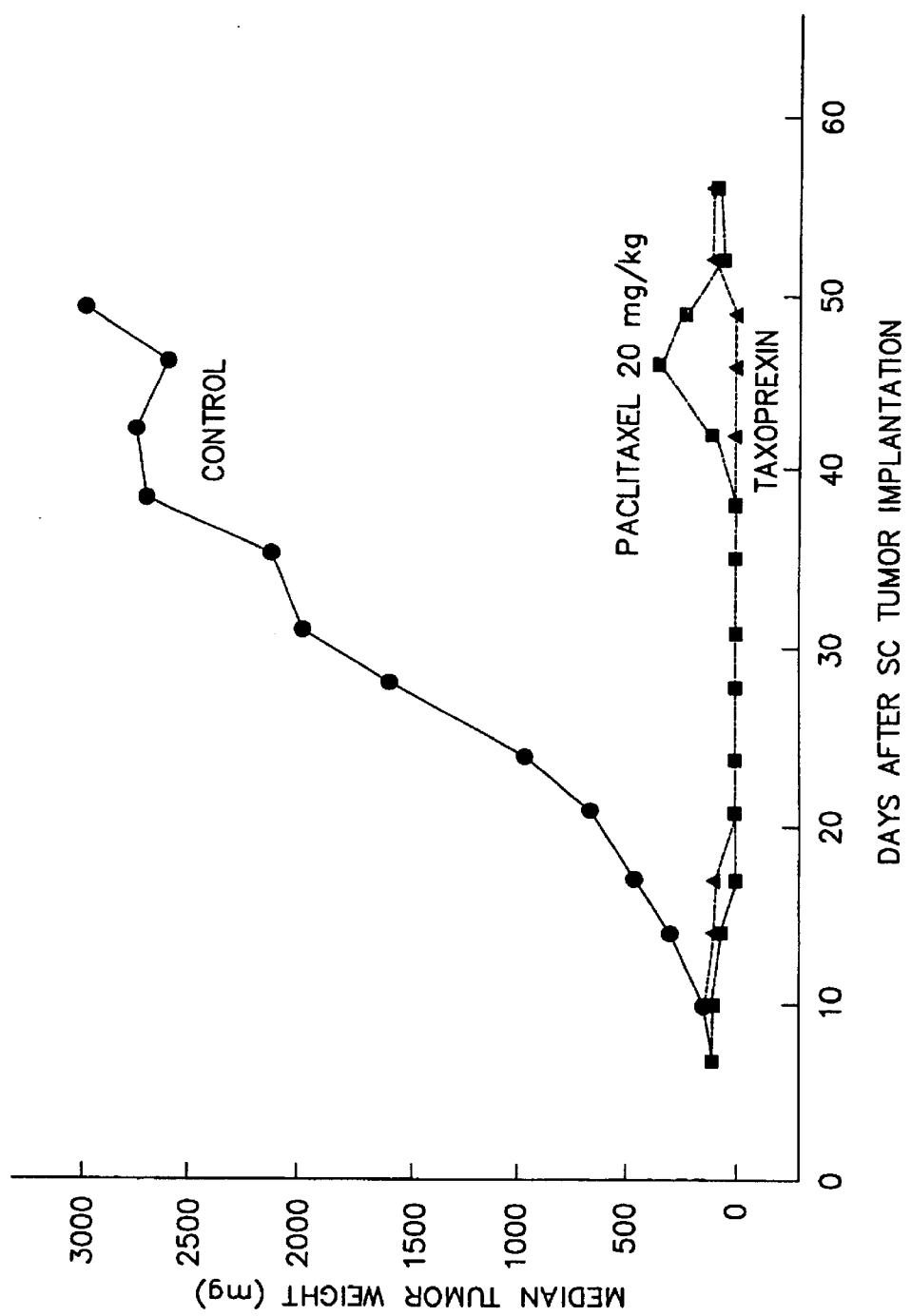
FIG. 3 is a graph depicting response of human NCI-H522 lung tumor to treatment with taxoprexin and paclitaxel in mice.

Response of Human NCI-H522 Lung Tumor to Treatment with Taxoprexin and Paclitaxel in Mice The Southern Research Institute studied the anti-tumor activity of taxoprexin against human NCI-H522 lung tumor growing in nude mice. The tumors were implanted subcutaneously. Tumor mass was determined by calculation from tumor length and width. The drugs were dissolved in 12.5% cremophor EL/12.5% ethanol/75% saline and delivered i.v. into the tail vein, once a day for 5 days, from day 15 to 19 after tumor implantation. The results show that taxoprexin at 50 mg/kg/day×5 days and paclitaxel at 20 mg/kg/day×5 days eliminated all measurable tumors in 10/10 mice. (FIG. 3)

EXAMPLE 4

The Pharmacokinetic Parameters of Taxoprexin and Paclitaxel

Rats were dosed for three minutes with 6.8 mg/kg of taxoprexin through the tail vein. The drug was dissolved in 10% cremaphor EL/10% ethanol/80% saline. The serum concentrations of both taxoprexin and paclitaxel were measured in a reverse phase HPLC assay. Pharmacokinetic parameters were calculated from these data. Taxoprexin has 100 fold lower clearance rate and volume of distribution. (FIG. 4)

EXAMPLE 5

Figure 5:
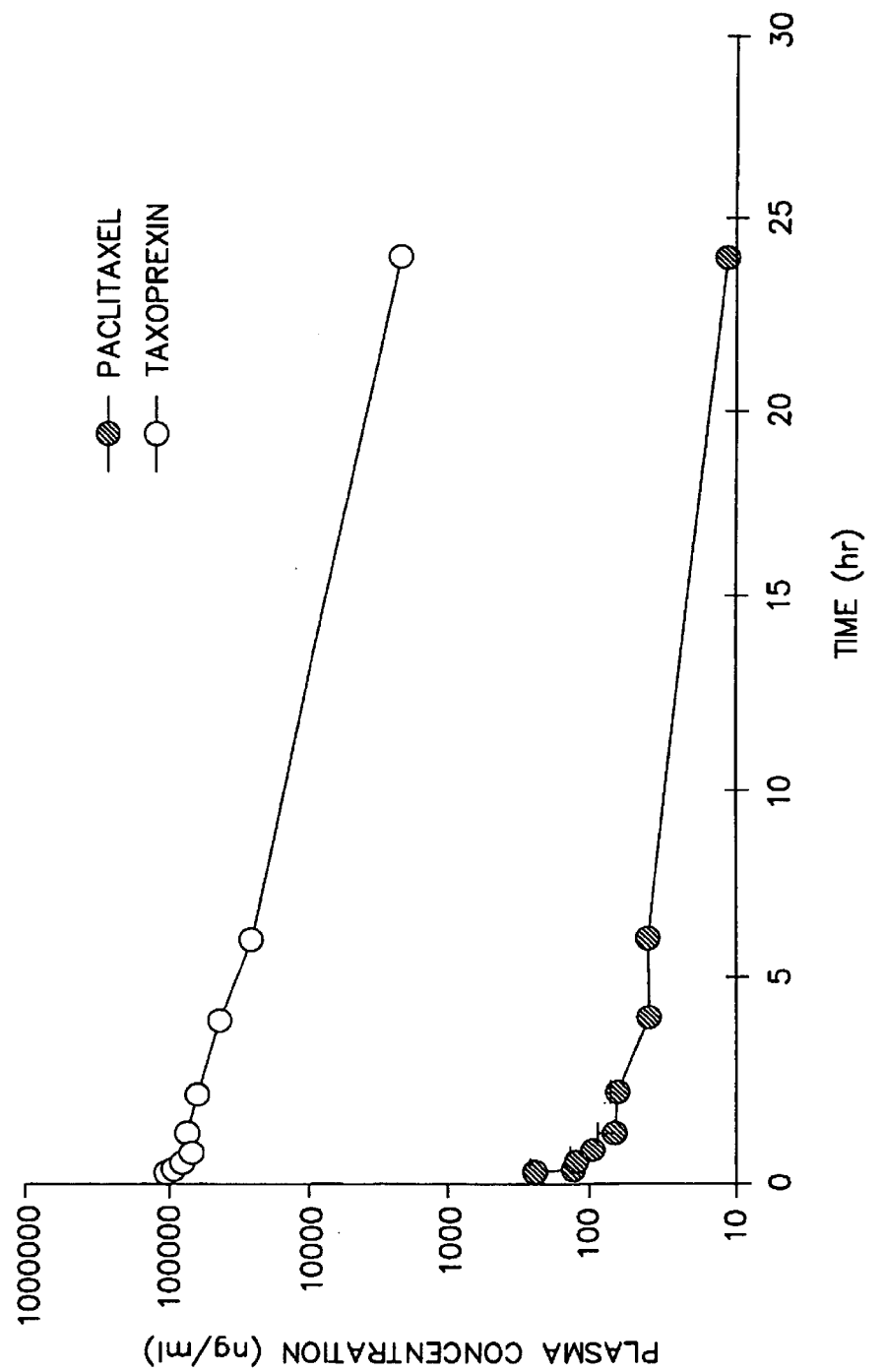
FIG. 5 is a graph depicting plasma concentration of taxoprexin and paclitaxel in rats following I.V. administrations of taxoprexin.
Figure 6:
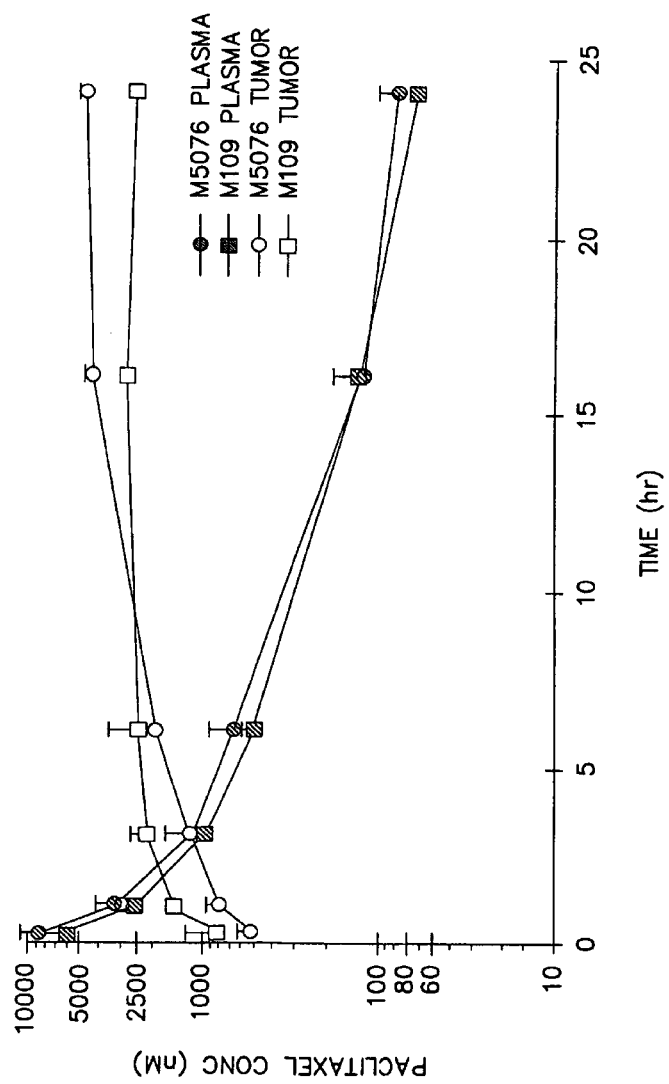
FIG. 6 is a graph depicting plasma and tumor concentrations of paclitaxel derived from an I.V. dose of 50 mg/kg of taxoprexin to mice bearing M 109 or M 5076 tumors.

Plasma Concentration of Taxoprexin and Paclitaxel in Rats Following I.V. Administrations of Taxoprexin Rats were given a 3 minute intravenous infusion of taxoprexin through the tail vein at 0 time. The drug was dissolved in 10% cremophor EL/10% ethanol/80% saline. The dose was 6.8 mg/kg. The concentrations in serum of both paclitaxel and taxoprexin as a function of time were measured in a reverse phase HPLC assay. (FIG. 5)

EXAMPLE 6

Plasma and Tumor Concentrations of Paclitaxel Derived from an I.V. Dose of 50 mg/kg of Taxoprexin to Mice Bearing M 109 or M 5076 Tumors Mice with tumors derived from M109 or M5076 were given a bolus does of taxoprexin through the tail vein at 0 time. The drug was dissolved in 10% cremophor EL/10% ethanol/80% saline. Mice were sacrificed and tumors immediately excised as a function of time after injecting the drug. Tumor tissue was homogenized and paclitaxel extracted. The concentration of paclitaxel was measured in a reverse phase HPLC assay. Blood was collected at the same time intervals and the amount of paclitaxel determined. The results show that after 24 hours the concentration of paclitaxel derived from taxoprexin is about 3 μM, 40 times higher than the plasma concentration, 70 nM. Each data point is the mean of three measurements (n=3); the error bar is one standard deviation. NOTE: Paclitaxel has a $t_{1/2}$ of <8 hours in the same tumor system.

EXAMPLE 7

Dose Comparisons (MTD and Est $LD_{40}$) of Taxoprexin and Paclitaxel in Various Species Dose comparisons for paclitaxel and taxoprexin were made in mice, rats and dogs. The maximum tolerated dose (MTD) for mice, rats and dogs were about 4–5 times higher for taxoprexin than for paclitaxel on a mg/kg basis, or 3–3.5 times higher on a molar paclitaxel equivalent basis. Dose limiting toxicity for rats and dogs is due to decreases in platelets, neutrophils and lymphocytes. Taxoprexin is less toxic to mice, rats and dogs than is paclitaxel.

The foregoing data establish, surprisingly, safety implications of dose and pharmacokinetic advantages of taxoprexin. The higher MTD of taxoprexin compared to paclitaxel is believed to lead to greater safety of taxoprexin with much greater efficacy. The smaller volume of distribution for taxoprexin is believed to lead to less damage by taxoprexin in peripheral tissues including, but not limited to, nerves, hair follicles, GI cells, etc. The longer residence time of taxoprexin in tumors is believed to lead to fewer required dosing cycles for optimum therapeutic efficacy, which is believed to lead to decreased systemic toxicity. Taxoprexin thus appears to have a 100 fold lower clearance rate and volume of distribution than paclitaxel. In addition, levels of paclitaxel in tumors treated with taxoprexin remain stable for 24 hours, whereas such levels in tumors treated with paclitaxel have stable levels for less than 8 hours. Finally, taxoprexin was shown to cure 3/8 mice of the human HCT colon tumor, while paclitaxel cured 0/8. HCT is a paclitaxel resistant tumor.

DHA and other naturally occurring, unbranched fatty acids may be conjugated to virtually any anti-cancer compound and used according to the methods of the present invention. Those of ordinary skill in the art will recognize also numerous other compounds that fall within the categories and that are useful according to the invention.

Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b ; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batirmastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epithilones, epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide;, lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Antiproliferative agent: Piritrexim Isethionate.

Antiprostatic hypertrophy: Sitogiuside.

Benign prostatic hyperplasia therapy agent: Tamsulosin Hydrochloride.

Prostate growth inhibitor: Pentomone.

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125 Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131 Iotyrosine 1 131; Liothyronine I 125; Liothyronine I 131; Merisoprol Acetate Hg 197; Merisoprol Acetate Hg 203; Merisoprol Hg 197; Selenomethionine Se 75; Technetium Tc 99 m Antimony Trisulfide Colloid; Technetium Tc 99 m Bicisate ; Technetium Tc 99 m Disofenin; Technetium Tc 99 m Etidronate ; Technetium Tc 99 m Exametazime ; Technetium Tc 99 m Furifosmin; Technetium Tc 99 m Gluceptate; Technetium Tc 99 m Lidofenin; Technetium Tc 99 m Mebrofenin ; Technetium Tc 99 m Medronate ; Technetium Tc 99 m Medronate Disodium; Technetium Tc 99 m Mertiatide ; Technetium Tc 99 m Oxidronate ; Technetium Tc 99 m Pentetate; Technetium Tc 99 m Pentetate Calcium Trisodium; Technetium Tc 99 m Sestamibi; Technetium Tc 99 m Siboroxime ; Technetium Tc 99 m Succimer ; Technetium Tc 99 m Sulfur Colloid; Technetium Tc 99 m Teboroxime; Technetium Tc 99 m Tetrofosmin; Technetium Tc 99 m Tiatide; Thyroxine 1 125; Thyroxine 1 131; Tolpovidone 1 131; Triolein 1 125; Triolein 1 131.

The invention also embraces novel compositions of matter that are covalent conjugates of unbranched, naturally occurring fatty acids and pharmaceutical agents.

As used herein, a taxane is a molecule that possesses a tricyclic carbon-atom connectivity network, which may incorporate carbon-carbon multiple bonds, and which through the involvement of carbon-atom-noncarbon-atom bonds may include substituents, functional groups, and additional rings. The structure of taxanes, as used herein, is shown in U.S. Pat. No. 5,795,909.

A taxoid is a molecule structurally related to a taxane in which the above taxane carbon-atom connectivity network is altered, for example, by cleavage of one or more of the carbocyclic rings, by deletion or addition of carbon substituents, by connection of carbon atoms normally not bonded to each other, by disconnection of carbon atoms normally bonded to each other, or by some other reorganization of or adjustment to the taxane carbon-atom connectivity network, but in which one or more structural features characteristic of the taxane carbon-atom connectivity network are conserved.

The compounds useful in the invention may be delivered in the form of anti-cancer cocktails. An anti-cancer cocktail is a mixture of any one of the compounds useful with this invention with another anti-cancer agent such as an anti-cancer drug, a cytokine, and/or supplementary potentiating agent(s). The use of cocktails in the treatment of cancer is routine. In this embodiment, a common administration vehicle (e.g., pill, tablet, implant, injectable solution, etc.) would contain both the conjugate useful in this invention and the anti-cancer drug and/or supplementary potentiating agent.

The compounds of the invention, when used alone or in cocktails, are administered in therapeutically effective amounts. A therapeutically effective amount will be determined by the parameters discussed below; but, in any event, is that amount which establishes a level of the drug(s) in the area of the tumor which is effective in inhibiting the tumor growth.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be a pharmaceutical composition having a therapeutically effective amount of a conjugate of the invention optionally included in a pharmaceutically-acceptable carrier. The term "pharmaceutically-acceptable carrier" as used herein means one or more compatible solid or liquid filler, diluents or encapsulating substances which are suitable for administration to a human or other animal. The term "carrier" denotes an organic or inorganic ingredient, natural or synthetic, with which the active ingredient is combined to facilitate the application. The components of the pharmaceutical compositions are capable of being commingled with the molecules of the present invention, and with each other, in a manner such that there is no interaction which would substantially impair the desired pharmaceutical efficacy.

Compositions suitable for parenteral administration conveniently comprise a sterile preparation of the conjugates of the invention. This preparation may be formulated according to known methods. Formulations for taxanes can be found in Chapter 9 of *Taxol: Science and Applications*, CRC Press, Inc., 2000 Corporate Boulevard, N.W., Boca Raton, Fla. 33431. In general, Taxol has been formulated as a 6 mg/ml Cremophor EL® (polyoxyethylated castor oil)/ethanol mixture, which is diluted to final volume with normal saline or 5% dextrose. A 15 mg/ml solution of Taxotere has been formulated in polysorbate 80 (polyoxyethylene sorbitanmonooleate)/ethanol mixture, diluted with 5% dextrose. This is in contrast to the formulations described herein.

The sterile preparation thus may be a sterile solution or suspension in a non-toxic parenterally-acceptable diluent or solvent. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in *Remington's Pharmaceutical Sciences*, Mack Publishing Company, Easton, Pa.

A subject as used herein means humans, primates, horses, cows, pigs, sheep, goats, dogs, cats and rodents.

The conjugates of the invention are administered in effective amounts. An effective amount means that amount necessary to delay the onset of, inhibit the progression of, halt altogether the onset or progression of or diagnose the particular condition being treated. In general, an effective amount for treating cancer will be that amount necessary to inhibit mammalian cancer cell proliferation in-situ. When administered to a subject, effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is, the highest safe dose according to sound medical judgment.

Dosage may be adjusted appropriately to achieve desired drug levels, locally or systemically. Generally, daily oral doses of active compounds will be from about 0.01 mg/kg per day to 1000 mg/kg per day. It is expected that IV doses in the range of about 1 to 1000 mg/m$^2$ per day will be effective. In the event that the response in a subject is insufficient at such doses, even higher doses (or effective higher doses by a different, more localized delivery route) may be employed to the extent that patient tolerance permits. Continuous IV dosing over, for example 24 hours or multiple doses per day are contemplated to achieve appropriate systemic levels of compounds. Preferred dosing schedules, including concentration, length of administration, and the like are described herein.

A variety of administration routes are available. The particular mode selected will depend of course, upon the particular drug selected, the severity of the disease state being treated and the dosage required for therapeutic efficacy. The methods of this invention, generally speaking, maybe practiced using any mode of administration that is medically acceptable, meaning any mode that produces effective levels of the active compounds without causing clinically unacceptable adverse effects. Such modes of administration include oral, rectal, sublingual, topical, nasal, transdermal, intradermal or parenteral routes. The term "parenteral" includes subcutaneous, intravenous, intramuscular, or infusion. Intravenous routes are preferred.

The compositions may conveniently be presented in unit dosage form and may be prepared by any of the methods well known in the art of pharmacy. All methods include the step of bringing the conjugates of the invention into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as potylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating solid tumors by placing the implant near or directly within the tumor, thereby affecting localized, high-doses of the compounds of the invention.

The conjugates of the invention also are useful, in general, for treating mammalian cell proliferative disorders other than cancer, including psoriasis, actinic keratosis, etc. They further are useful in treating diabetes and its complications, excess acid secretion, cardiovascular conditions involving cholesterol (e.g., hyperlipidemia and hypercholesterolemia), diarrhea, ovarian diseases (e.g. endometriosis, ovarian cysts, etc.) and as contraceptive agents.

Those skilled in the art will be able to recognize with no more than routine experimentation numerous equivalents to the specific products and processes described above. Such equivalents are intended to be included within the scope of the appended claims.

All references disclosed herein are incorporated by reference.

We claim as follows:

1. A fatty acid-anticancer compound conjugate composition for administration to a subject, comprising at least one fatty acid-anticancer compound conjugate in a container for administration to a subject, wherein the amount of the fatty acid-anticancer compound in the container is at least about 30% on a molar basis greater than the maximum tolerated dose (MTD) in the subject for the unconjugated at least one anticancer compound, wherein the container is a container for intravenous administration.

2. The fatty acid-anticancer compound conjugate composition of claim 1, wherein the amount in the container is at least about 50% greater than the MTD for the unconjugated at least one anticancer compound.

3. The fatty acid-anticancer compound conjugate composition of claim 1, wherein the amount in the container is at least about 100% greater than the MTD for the unconjugated at least one anticancer compound.

4. The fatty acid-anticancer compound conjugate composition of claim 1, wherein the anticancer compound is a taxane.

5. A method for treating a subject having an abnormal mammalian cell proliferative disorder, comprising administering to the subject a fatty acid-anticancer compound conjugate composition in an amount which is at least about 30% on a molar basis greater than the maximum tolerated dose (MTD) in the subject for the unconjugated at least one anticancer compound.

6. The method of claim 5, wherein the amount of the fatty acid-anticancer compound conjugate composition administered is at least about 50% greater than the MTD for the unconjugated at least one anticancer compound.

7. The method of claim 5, wherein the amount of the fatty acid-anticancer compound conjugate composition administered is at least about 100% greater than the MTD for the unconjugated at least one anticancer compound.

8. The method of claim 5, wherein the anticancer compound is a taxane.

9. A kit for administration of a fatty acid-anticancer compound conjugate composition to a subject, comprising
   a container containing at least one fatty acid-anticancer compound conjugate, and
   instructions for administering the at least one fatty acid-anticancer compound conjugate to subject in need of such treatment in an amount which is at least about 30% on a molar basis greater than the maximum tolerated dose (MTD) in the subject for the unconjugated at least one anticancer compound.

10. An injectable preparation of at least one fatty acid-taxane conjugate composition, comprising greater than about 6 mg/ml of the at least one fatty acid-taxane conjugate composition.

11. The injectable preparation of claim 10, wherein the preparation comprises greater than about 20 mg/ml of the at least one fatty acid-taxane conjugate composition.

12. The injectable preparation of claim 10, wherein the preparation comprises greater than about 80 mg/ml of the at least one fatty acid-taxane conjugate composition.

13. An injectable composition of at least one fatty acid-taxane conjugate in a polyoxyethylated castor oil, comprising less than about 0.3 mg/ml of the at least one fatty acid-taxane conjugate.

14. A fatty acid-taxane conjugate composition, comprising greater than about 6 mg/ml of at least one fatty acid-taxane conjugate, and a surfactant.

15. The fatty acid-taxane conjugate composition of claim 14, wherein the amount of the at least one fatty acid-taxane conjugate is greater than about 20 mg/ml.

16. The fatty acid-taxane conjugate composition of claim 14, wherein the amount of the at least one fatty acid-taxane conjugate is greater than about 80 mg/ml.

17. The fatty acid-taxane conjugate composition of claim 14, wherein the surfactant is a polyoxyethylated castor oil.

18. A fatty acid-taxane conjugate composition, comprising at least one fatty acid-taxane conjugate and a surfactant, wherein the ratio of the weight of the at least one fatty acid-taxane conjugate and volume of the surfactant is at least about 50 mg/ml.

19. The fatty acid-taxane conjugate composition of claim 18, wherein the ratio of the weight of the at least one fatty acid-taxane conjugate and volume of the surfactant is at least about 100 mg/ml.

20. The fatty acid-taxane conjugate composition of claim 18, wherein the surfactant is a polyoxyethylated castor oil.

21. The fatty acid-taxane conjugate composition of claim 18, further comprising a solvent.

22. A fatty acid-taxane conjugate composition, comprising at least one fatty acid-taxane conjugate and a solvent, wherein the ratio of the weight of the at least one fatty acid-taxane conjugate and volume of the solvent is at least about 42 mg/ml.

23. The fatty acid-taxane conjugate composition of claim 22, wherein the ratio of the weight of the at least one fatty acid-taxane conjugate and volume of the solvent is at least about 80 mg/ml.

24. The fatty acid-taxane conjugate composition of claim 22, wherein the solvent is a polyoxyethylated castor oil.

25. The fatty acid-taxane conjugate composition of claim 22, further comprising a surfactant.

26. The fatty acid-taxane conjugate composition of claim 25, wherein the surfactant is a polyoxyethylated castor oil.

27. A fatty acid-taxane conjugate composition, comprising at least about 37 mg/ml of at least one fatty acid-taxane conjugate.

28. The fatty acid-taxane conjugate composition of claim 27, wherein the amount of the at least one fatty acid-taxane conjugate is least about 80 mg/ml.

29. The fatty acid-anticancer compound conjugate composition of claim 1, wherein the amount in the container is at least about 40% greater than the MTD for the unconjugated at least one anticancer compound.

30. The fatty acid-anticancer compound conjugate composition of claim 1, wherein the amount in the container is at least about 75% greater than the MTD for the unconjugated at least one anticancer compound.

31. The fatty acid-anticancer compound conjugate composition of claim 1, wherein the container is a container for intravenous administration.

32. The fatty acid-anticancer compound conjugate composition of claim 4, wherein the taxane is paclitaxel or docetaxel.

33. The fatty acid-anticancer compound conjugate composition of claim 1, wherein the conjugate is not encapsulated in a liposome.

34. The fatty acid-anticancer compound conjugate composition of claim 1, wherein the fatty acid is docosahexaenoic acid.

35. The method of claim 5, wherein the amount of the fatty acid-anticancer compound conjugate composition administered is at least about 40% greater than the MTD for the unconjugated at least one anticancer compound.

36. The method of claim 5, wherein the amount of the fatty acid-anticancer compound conjugate composition administered is at least about 75% greater than the MTD for the unconjugated at least one anticancer compound.

37. The method of claim 8, wherein the taxane is paclitaxel or docetaxel.

38. The method of claim 5, wherein the conjugate is not encapsulated in a liposome.

39. The method of claim 5, wherein the fatty acid is docosahexaenoic acid.

40. The kit of claim 9, wherein the amount of the at least one fatty acid-anticancer compound conjugate is at least about 40% greater than the MTD for the unconjugated at least one anticancer compound.

41. The kit of claim 9, wherein the amount of the at least one fatty acid-anticancer compound conjugate is at least about 75% greater than the MTD for the unconjugated at least one anticancer compound.

42. The kit of claim 9, wherein the at least one fatty acid-anticancer compound conjugate is a taxane.

43. The kit of claim 42, wherein the taxane is paclitaxel or docetaxel.

44. The kit of claim 9, wherein the conjugate is not encapsulated in a liposome.

45. The kit of claim 9, wherein the fatty acid is docosohexaenoic acid.

46. A method for increasing the therapeutic index of anticancer compounds in a subject, comprising:
    conjugating a fatty acid to an anticancer compound to form a fatty acid-anticancer compound conjugate; and
    administering the fatty acid-anticancer compound conjugate to the subject, whereby the therapeutic index of the anticancer compound is improved relative to non-conjugated formulations of the anticancer compound, and wherein the fatty acid-anticancer compound conjugate is in an amount which is at least about 30% on a molar basis greater than the maximum tolerated dose (MTD) in the subject for the non-conjugated anticancer compound.

47. The method of claim 46, wherein the anticancer compound is a taxane.

48. The method of claim 47, wherein the taxane is paclitaxel or docetaxel.

49. The method of claim 46, wherein the conjugate is not encapsulated in a liposome.

50. The method of claim 46, wherein the fatty acid is a C8–C26 unbranched, naturally occurring fatty acid.

51. The method of claim 50, wherein the fatty acid is docosohexaenoic acid.

52. The method of claim 46, wherein the subject is human.

53. A method for administering a fatty acid-taxane conjugate to a subject in need of such treatment, comprising infusing the conjugate in fewer than 3 hours.

54. The method of claim 53, wherein the conjugate is infused in 2 hours or less.

55. The injectable preparation of claim 10, wherein the preparation comprises greater than about 7 mg/ml of the at least one fatty acid-taxane conjugate composition.

56. The injectable preparation of claim 10, wherein the preparation comprises greater than about 8 mg/ml of the at least one fatty acid-taxane conjugate composition.

57. The injectable preparation of claim 10, wherein the preparation comprises greater than about 10 mg/ml of the at least one fatty acid-taxane conjugate composition.

58. The injectable preparation of claim 10, wherein the preparation comprises greater than about 15 mg/ml of the at least one fatty acid-taxane conjugate composition.

59. The injectable preparation of claim 10, wherein the preparation comprises greater than about 40 mg/ml of the at least one fatty acid-taxane conjugate composition.

60. The injectable preparation of claim 10, wherein the preparation comprises greater than about 60 mg/ml of the at least one fatty acid-taxane conjugate composition.

61. The injectable preparation of claim 10, wherein the preparation comprises greater than about 100 mg/ml of the at least one fatty acid-taxane conjugate composition.

62. The injectable preparation of claim 10, wherein the fatty acid is a C8–C26 unbranched, naturally occurring fatty acid.

63. The injectable preparation of claim 62, wherein the fatty acid is docosohexaenoic acid.

64. The fatty acid-taxane conjugate composition of claim 14, wherein the amount of the at least one fatty acid-taxane conjugate is greater than about 7 mg/ml.

65. The fatty acid-taxane conjugate composition of claim 14, wherein the amount of the at least one fatty acid-taxane conjugate is greater than about 8 mg/ml.

66. The fatty acid-taxane conjugate composition of claim 14, wherein the amount of the at least one fatty acid-taxane conjugate is greater than about 10 mg/ml.

67. The fatty acid-taxane conjugate composition of claim 14, wherein the amount of the at least one fatty acid-taxane conjugate is greater than about 15 mg/ml.

68. The fatty acid-taxane conjugate composition of claim 14, wherein the amount of the at least one fatty acid-taxane conjugate is greater than about 40 mg/ml.

69. The fatty acid-taxane conjugate composition of claim 14, wherein the amount of the at least one fatty acid-taxane conjugate is greater than about 60 mg/ml.

70. The fatty acid-taxane conjugate composition of claim 14, wherein the amount of the at least one fatty acid-taxane conjugate is greater than about 100 mg/ml.

71. The fatty acid-taxane conjugate composition of claim 14, wherein the fatty acid is a C8–C26 unbranched, naturally occurring fatty acid.

72. The fatty acid-taxane conjugate composition of claim 71, wherein the fatty acid is docosohexaenoic acid.

73. The fatty acid-taxane conjugate composition of claim 17, wherein the concentration of Cremophor is between about 9.6% and about 49.7% (vol/vol).

74. The fatty acid-taxane conjugate composition of claim 18, wherein the ratio of the weight of the at least one fatty acid-taxane conjugate and volume of the surfactant is at least about 60 mg/ml.

75. The fatty acid-taxane conjugate composition of claim 18, wherein the ratio of the weight of the at least one fatty acid-taxane conjugate and volume of the surfactant is at least about 70 mg/ml.

76. The fatty acid-taxane conjugate composition of claim 18, wherein the ratio of the weight of the at least one fatty acid-taxane conjugate and volume of the surfactant is at least about 80 mg/ml.

77. The fatty acid-taxane conjugate composition of claim 18, wherein the ratio of the weight of the at least one fatty acid-taxane conjugate and volume of the surfactant is at least about 90 mg/ml.

78. The fatty acid-taxane conjugate composition of claim 18, wherein the fatty acid is a C8–C26 unbranched, naturally occurring fatty acid.

79. The fatty acid-taxane conjugate composition of claim 78, wherein the fatty acid is docosahexaenoic acid.

80. The fatty acid-taxane conjugate composition of claim 18, wherein the taxane is paclitaxel or docetaxel.

81. The fatty acid-taxane conjugate composition of claim 21, wherein the solvent is ethanol.

82. The fatty acid-taxane conjugate composition of claim 81, wherein the solvent and the surfactant are present in a ratio of about 1:1.

83. The fatty acid-taxane conjugate composition of claim 22, wherein the ratio of the weight of the at least one fatty acid-taxane conjugate and volume of the solvent is at least about 50 mg/ml.

84. The fatty acid-taxane conjugate composition of claim 22, wherein the ratio of the weight of the at least one fatty acid-taxane conjugate and volume of the solvent is at least about 60 mg/ml.

85. The fatty acid-taxane conjugate composition of claim 22, wherein the ratio of the weight of the at least one fatty acid-taxane conjugate and volume of the solvent is at least about 70 mg/ml.

86. The fatty acid-taxane conjugate composition of claim 22, wherein the ratio of the weight of the at least one fatty acid-taxane conjugate and volume of the solvent is at least about 100 mg/ml.

87. The fatty acid-taxane conjugate composition of claim 22, wherein the fatty acid is a C8–C26 unbranched, naturally occurring fatty acid.

88. The fatty acid-taxane conjugate composition of claim 87, wherein the fatty acid is docosahexaenoic acid.

89. The fatty acid-taxane conjugate composition of claim 22, wherein the taxane is paclitaxel or docetaxel.

90. The fatty acid-taxane conjugate composition of claim 26, wherein the solvent and the surfactant are present in a ratio of about 1:1.

91. The fatty acid-taxane conjugate composition of claim 27, wherein the amount of the at least one fatty acid-taxane conjugate is least about 40 mg/ml.

92. The fatty acid-taxane conjugate composition of claim 27, wherein the amount of the at least one fatty acid-taxane conjugate is least about 50 mg/ml.

93. The fatty acid-taxane conjugate composition of claim 27, wherein the amount of the at least one fatty acid-taxane conjugate is least about 60 mg/ml.

94. The fatty acid-taxane conjugate composition of claim 27, wherein the amount of the at least one fatty acid-taxane conjugate is least about 100 mg/ml.

95. The fatty acid-taxane conjugate composition of claim 27, wherein the fatty acid is a C8–C26 unbranched, naturally occurring fatty acid.

96. The fatty acid-taxane conjugate composition of claim 27, wherein the fatty acid is docosahexaenoic acid.

97. The fatty acid-taxane conjugate composition of claim 27, wherein the taxane is paclitaxel or docetaxel.

* * * * *